US005906586A

United States Patent [19]
Graham

[11] Patent Number: 5,906,586
[45] Date of Patent: May 25, 1999

[54] VECTORED PNEUMATIC JOINT SEPARATOR

[76] Inventor: Richard A. Graham, 18582 Main St., Huntington Beach, Calif. 92648

[21] Appl. No.: 09/010,954

[22] Filed: Jan. 22, 1998

[51] Int. Cl.⁶ .................................................. A61F 5/00
[52] U.S. Cl. .......................... 602/32; 128/845; 601/148; 602/13; 602/35; 297/284.6
[58] Field of Search ................... 602/32–36, 38, 602/13; 601/148, 149, 151, 152, 23; 606/240, 241; 128/DIG. 19, DIG. 20, 845; 297/284.6, 452.41; 5/655.3, 653, 654

[56] References Cited

U.S. PATENT DOCUMENTS

| | | |
|---|---|---|
| Re. 32,791 | 11/1988 | Saunders . |
| 3,667,457 | 6/1972 | Zumaglini . |
| 3,765,412 | 10/1973 | Ommaya et al. . |
| 3,899,797 | 8/1975 | Gunst ...................................... 297/456 |
| 3,974,827 | 8/1976 | Bodeen . |
| 4,024,861 | 5/1977 | Vincent . |
| 4,114,611 | 9/1978 | Lyle et al. . |
| 4,391,466 | 7/1983 | Smith ...................................... 297/452 |
| 4,583,255 | 4/1986 | Mogaki et al. ............................. 5/453 |
| 4,669,455 | 6/1987 | Bellati . |
| 4,838,613 | 6/1989 | Smith ...................................... 297/452 |
| 4,981,131 | 1/1991 | Hazard . |
| 5,067,483 | 11/1991 | Freed . |
| 5,147,287 | 9/1992 | Jewell et al. ............................... 602/32 |
| 5,154,186 | 10/1992 | Laurin et al. . |
| 5,181,904 | 1/1993 | Cook et al. ................................ 602/32 |
| 5,190,348 | 3/1993 | Colasanti ............................... 297/284.6 |
| 5,201,761 | 4/1993 | Serola ...................................... 606/240 |
| 5,207,716 | 5/1993 | McReynolds et al. . |
| 5,211,162 | 5/1993 | Gillen, Jr. et al. ....................... 601/149 |
| 5,279,310 | 1/1994 | Hsien . |
| 5,292,175 | 3/1994 | Artz ...................................... 297/250.1 |
| 5,305,750 | 4/1994 | Makita . |
| 5,338,276 | 8/1994 | Jull et al. ................................... 601/23 |
| 5,382,226 | 1/1995 | Graham ...................................... 602/32 |
| 5,403,266 | 4/1995 | Bragg et al. ................................. 602/5 |
| 5,410,472 | 4/1995 | Anderson ............................ 364/413.04 |
| 5,423,861 | 6/1995 | Kelley ...................................... 606/241 |
| 5,472,401 | 12/1995 | Rouillard et al. ........................ 482/142 |
| 5,560,056 | 10/1996 | Tai .............................................. 5/120 |
| 5,562,324 | 10/1996 | Massara et al. ....................... 297/284.6 |
| 5,772,281 | 6/1998 | Massara ................................ 297/284.4 |

FOREIGN PATENT DOCUMENTS

| | | | |
|---|---|---|---|
| 2638077 | 3/1977 | Germany ................................. 602/32 |
| 404327849 | 11/1992 | Japan ...................................... 601/148 |
| 8700424 | 1/1987 | WIPO ...................................... 602/32 |

Primary Examiner—Richard J. Apley
Assistant Examiner—Justine R. Yu
Attorney, Agent, or Firm—Walter A. Hackler

[57] ABSTRACT

A spinal joint separator device and method for exercising a spine to promote spinal health are provided. The device may generally include a frame and a first and a second bladder secured to the frame for separating vertebrae in the spine in order to promote fluid imbibition therethrough. The bladders provide diverging directions of force against a lordotic arc in the spine of a user, for example against the lumbar or cervical spine. When in an uninflated state the second bladder is disposed on the frame such that it overlaps the first bladder. In addition, a pump and valve may be provided for allowing independent and sequential inflation of the bladders. In accordance with a method of the invention, the first bladder may be inflated against the spine in a first direction to lift and hold the spine in a lordotic arc. Subsequently, the second bladder is inflated against the spine in a second direction to further lift the spine, stretch the spine linearly and gently separate the vertebrae. Both bladders may be further inflated to increase and elongate the lordotic arc, promote cellular and fluid exchange about the vertebrae as well as reinstate a lordotic arc and longitudinal alignment of vertebrae in the spine.

7 Claims, 2 Drawing Sheets

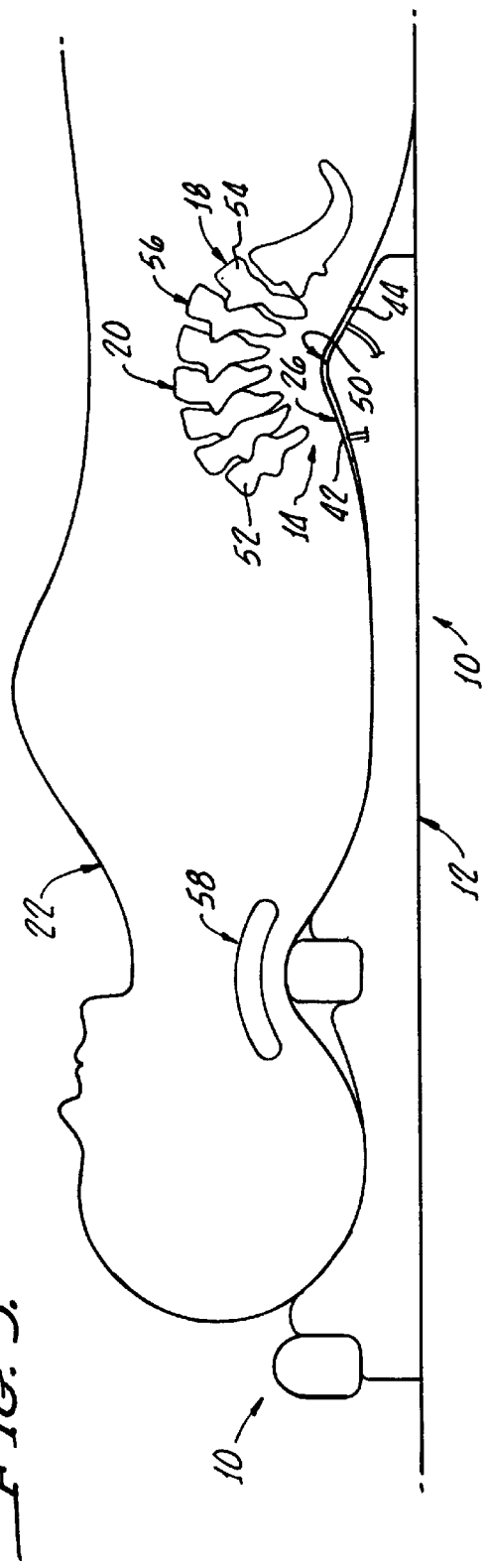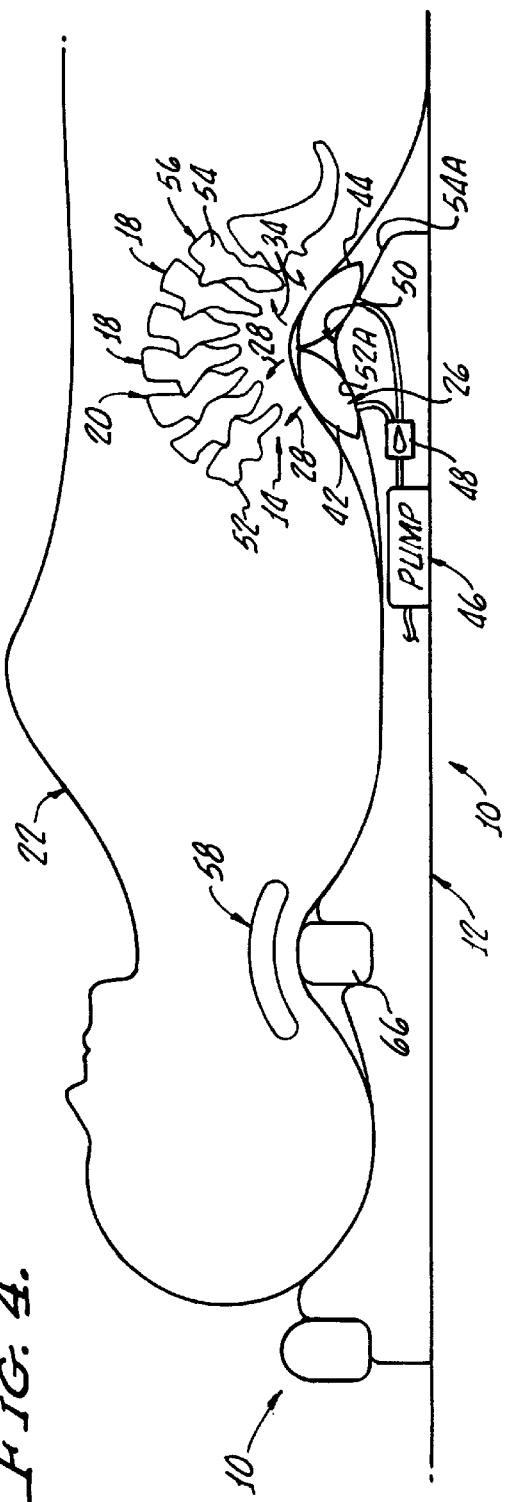

VECTORED PNEUMATIC JOINT SEPARATOR

The present invention relates to a device for separating vertebrae in a spinal column and more specifically relates to a vectored pneumatic joint separator and method for promoting fluid imbibition through the spinal column.

The spinal column is a bony column forming the main structural support of the skeleton of a human being and it consists of bony vertebrae linked by flexible joints and held together by ligaments and flexible gelatinous discs of cartilage. The spinal column of an adult human being consists of thirty three vertebrae, in which the last nine of these are fused to form the sacrum and the coccyx at the back of the pelvis. It is known that the spine has a number of curvatures along the sagittal plane, namely, the cervical and lumbar curvatures in which the spine is convex toward the front of the body and the dorsal and sacral curvatures in which the spine is convex toward the back of the body. These alternating curves provide strength and balance to the body and are essential to allowing a person to walk upright.

The lumbar and cervical curves of the spine normally define forward curves of about 35 to about 45 degrees whereby weight is distributed relatively evenly on individual vertebral surfaces and discs. In individuals with lost or reversed cervical and lumbar spinal curves due to injury, illness, genetic predisposition, habitual microtrauma or simply poor posture, the weight of the body bears forwardly on the soft, non-bony intervertebral discs, inhibiting fluid transfer and causing the discs to wear, dehydrate and degenerate. Over time, these individuals exhibit a significant loss of natural joint movement. Lack of natural movement in the spine over time causes a reduction in the imbibition of nutrient rich fluids that normally lubricate and maintain flexibility of the spine. Without this seepage of fluids into the spinal column, the discs will further dehydrate, which may result in further loss of mobility, crippling and possible nerve damage. It is further noted that the intervertebral discs' indigenous vascular fluid supply disappears at approximately 20 years of age. Thus, active nutrient transport of fluids surrounding the spinal column is particularly important to maintaining spinal health of adults.

In addition to spinal traction devices which are well known for stretching the spine longitudinally in order to restore lost mobility, devices have been developed for either passively or actively restoring the normal curves of the spine to prevent the disabling effects of lost or impaired curvature mentioned hereinabove. Passive devices include, for example, the Spinal Column Correction Device disclosed in U.S. Pat. No. 5,279,310 to Hsein. In this device, a user is strapped to a series of raised supports that define what the normal curvatures of the spine should be. According to the inventor, the weight of the user's body will bear against the raised supports to correct abnormal curvature in the spine. A useful device that actively exercises the normal lordotic, i.e. forward, curves of a spine is disclosed in U.S. Pat. No. 5,382,226 to Graham entitled Inflatable Cervical Traction and Exercising Device, this patent being incorporated herein by this specific reference thereto. In the Graham patent, a device is disclosed which utilizes an inflatable bladder for actively forcing the cervical spine into a forward curve. This exercising of the spine promotes fluid imbibition through the spinal vertebrae.

The present invention provides an improved device and method for maintaining spinal health which utilizes a dual action air chamber defining multiple vectors of force to be applied to a spine, particularly to the lumbar spinal region. The device gradually lifts and separates the vertebrae in a manner that surpasses the effectiveness and comfort of conventional traction devices and passive spinal correction devices.

SUMMARY OF THE INVENTION

Accordingly, in accordance with the present invention, a vectored pneumatic joint separator device is provided for promoting spinal health by actively exercising the spine and promoting fluid imbibition throughout the vertebrae and intervertebral discs. The device generally comprises a frame and means, secured to the frame, for separating vertebrae in a spinal column of a user. The frame may be adapted to receive the torso of a user in a reclined position on the frame.

More specifically, the means for separating include first means for bearing against the spine in a first direction, and second means, adjacent the first means, for bearing against the spine in a second direction, said first and said second directions being divergent along a sagittal plane of the user and concentrating a bearing force forward into the spinal column. Even more specifically, the first means may comprise a first inflatable bladder and the second means may comprise a second inflatable bladder, both bladders being adjacent one another and each providing different, diverging force vectors against the spine when a user is reclined or sitting on the frame.

Preferably, means are provided for enabling independent and sequential inflation of the bladders as well as simultaneous inflation of the bladders. In this respect, the second bladder may be disposed to partially overlap the first bladder when the bladders are in an uninflated state. This arrangement facilitates positioning of the second bladder for subsequent inflation in a direction divergent from the direction of inflation of the first bladder. Thus, initially, the first bladder may be partially inflated to contact and lift the spine in a lordotic arc shape. The second bladder may then be partially inflated to further lift the spine. Both bladders are then further inflated to increase and elongate the lordotic arc and promote fluid imbibition throughout the vertebrae and discs. During the further inflation of the bladders, the spine is linearly stretched causing longitudinal alignment of the spinal vertebrae. This sequential inflation may be repeated several times in a single therapy session for reinstating a lordotic arc in the spine as well as aligning the vertebrae along the longitudinal spinal axis. Accordingly, an object of the invention is to provide a device which will train the spine into its natural shape and lubricate the joints thereof.

In a broader aspect of the invention the means for separating vertebrae in the spine may include first means for applying a lifting force vector against the vertebrae in the spine, and second means for applying a separating force vector against the vertebrae in the spine, said separating force vector being in a direction away from the lifting force vector. The first and second bladders may be discussed briefly hereinabove may be inflated partially just enough to hold the spine in the lordotic arc, and may then be further inflated to actively force the spine into a greater, or hyper-lordotic arc and cause the desired separation of the vertebrae.

The present invention is to be distinguished from traction devices which "pull" the spine, typically along its longitudinal axis, and cause the vertebrae to stretch apart and separate without regard for the natural sagittal curvatures. In contrast, the present invention provides a force which bears against the spine, pushing the lumbar or cervical spine toward the front of the body using two diverging vectors of force to cause the joints along the spine to separate angularly and recover their natural arc.

The device described briefly hereinabove is suitable for performing a method, in accordance with the present invention, for exercising a spine to promote spinal health. More particularly, the method may include the steps of (a) separating vertebrae in the user's spine by sequentially inflating a first and second bladder against the spine and (b) promoting fluid imbibition throughout the vertebrae by allowing the vertebrae to remain separated for a selected time. The method may further include the step of (c) repeating steps (a) and (b) periodically or otherwise in a timely manner to actively exercise the spine. The two bladders are configured to provide different, diverging angles of force against the spine.

For maximum effectiveness and comfort to the user, initially the bladders are preferably only partially inflated to gently lift the spine into a lordotic arc. After this initial lifting, the bladders may be further inflated, up to full pressure, to increase the lordotic arc and angularly separate the vertebrae. The bladders may be held in the inflated state for a selected time period and then deflated completely to allow the spine to rest. The steps may be repeated on a timely basis during a single spinal therapy session.

BRIEF DESCRIPTION OF THE DRAWINGS

The present invention will be more readily understood in light of the following detailed description when considered in conjunction with the accompanying drawings of which:

FIG. 3 shows a diagrammatical side view of the device shown in FIGS. 1 and 2 in which a user is reclined on the device when the bladders are in an uninflated state; and FIG. 4 shows the diagrammatical side view of the device shown in FIG. 3 wherein the bladders have been inflated to force the user's spine into a lordotic arc and promote fluid imbibition throughout the spinal vertebrae and discs.

DETAILED DESCRIPTION

Figure 1:
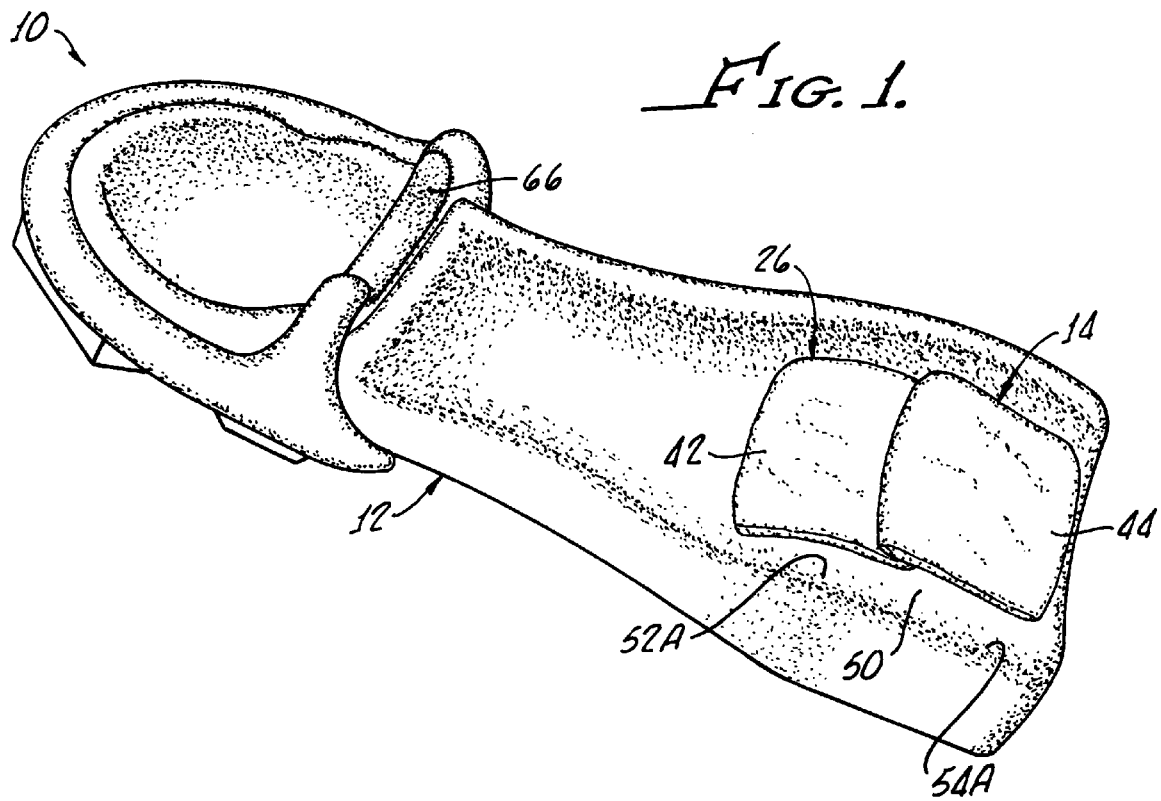
FIG. 1 shows a perspective view of a vectored pneumatic joint separator device in accordance with the present invention, including two inflatable bladders disposed on a frame, a second of the bladders overlapping a first of the bladders.
Figure 2:
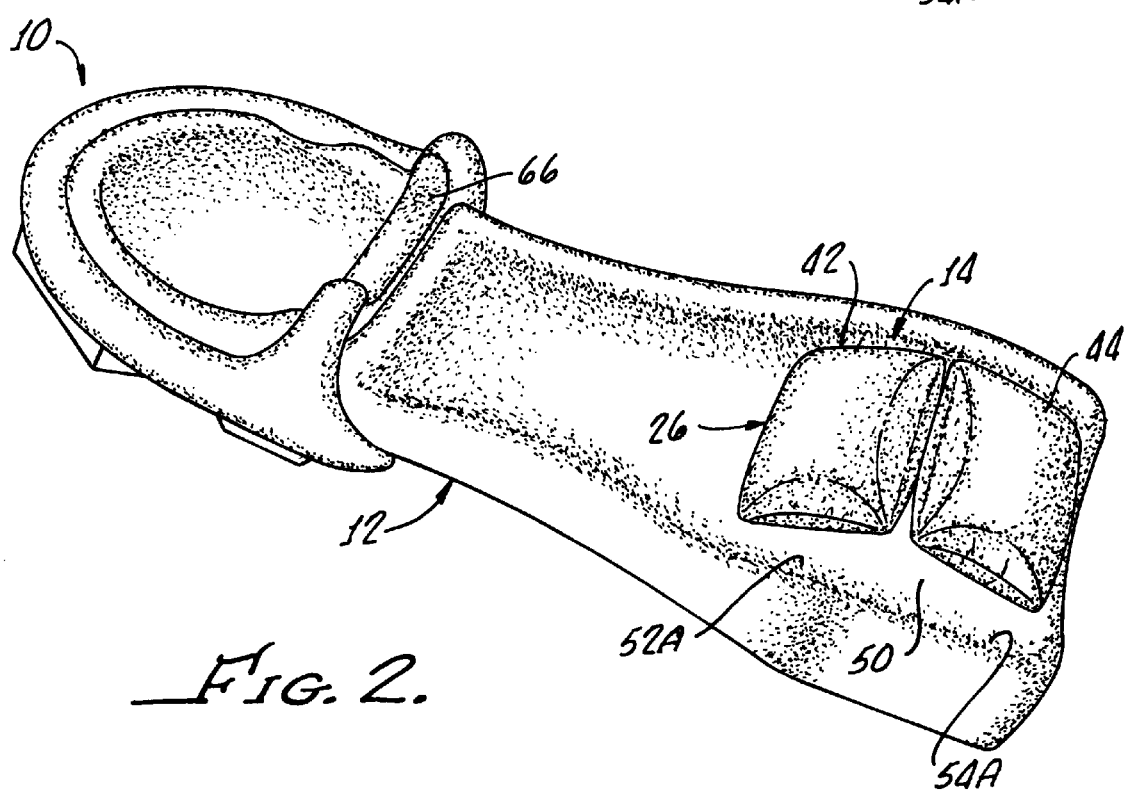
FIG. 2 shows the vectored pneumatic joint separator shown in FIG. 1 in which the two bladders have been inflated in order to provide two distinct vectors of force against a user's spine.

Turning now to FIGS. 1 and 2, a spinal joint separator device 10 in accordance with the invention is shown. Referring now as well to FIGS. 3 and 4, the device 10 may generally include a frame 12 and means 14 for separating vertebrae 18 in a spinal column 20 of a user 22 in order to promote fluid imbibition therethrough for maintaining or improving spinal health.

More particularly, as shown in FIGS. 3 and 4, the means 14 for separating the vertebrae 18 may comprise first means 26 for bearing against the spine 20 in a first direction represented by arrows 28 and second means 32, adjacent the first means 26, for bearing against the spine 20 in a second direction, represented by arrows 34, said first and second means 26, 32 being divergent along a sagittal plane of the user 22.

Even more particularly, the first means 26 and the second means 32 may comprise, respectively, a first inflatable bladder 42 and a second inflatable bladder 44. The bladders 42, 44 are preferably discrete air chambers, inflatable by a pump 46 or any other suitable arrangement. The bladders 42, 44 may be made of any suitable material.

Means, such as a valve 48, may be provided for enabling independent and sequential inflation of the bladders 42, 44 in addition to simultaneous inflation of the bladders 42, 44. Importantly, the bladders 42, 44 are configured and positioned to provide separate, distinct vectors of force against the spine 20, as shown by arrows 28 and 34. This may be accomplished by disposing the bladders on an arched projection 50 defined by the frame 12 as shown. As shown in FIG. 3 the arched projection 50 generally conforms to a curvature of the lower thoracic vertebrae 52 and lumbar vertebrae 54. More particularly,, the projection 50 includes a first surface 52A generally conforming to the lower thoracic vertebrae 52 curvature and a second surface 54A generally conforming to the lumber vertebrae 54 curvature. The first bladder 42 is disposed on the first surface 52A for directly bearing against the lower thoracic vertebrae 52 in a first direction 28 and the second bladder is disposed on the second surface 54A for directly bearing against the lumbar vertebrae 54 in a second direction 34. In addition, the second bladder 44 may be disposed partially over, or overlap the first bladder 42 when in an uninflated state (see FIG. 1). This will provide proper positioning of the bladders 42, 44 during the sequential inflation steps.

As will be discussed in greater detail, after a user 22 is comfortably reclined on the device 10 with his lumbar spine 56, for example, disposed over the bladders 42, 44, the first bladder 42 is partially inflated to a pressure sufficient for lifting the lumbar spine into a lordotic arc. The first bladder 42 provides means for accentuating a diminished lordotic arc in the lumbar spine region and causing angular separation of the vertebrae 18 in this region. During this partial inflation of the first bladder 42, the second bladder 44 is partially inflated to further lift the spine 20 and gently angularly separate the vertebrae further. By pressing the spine 20 in a direction divergent from the direction of pressure provided by the first bladder 42, the second bladder 44 provides means for linearly elongating the lordotic arc while the vertebrae 18 are angularly separated by the first bladder 42. Next, both bladders 42, 44 are fully and simultaneously inflated, which forces the spine 20 into an increased, or hyperlordotic, arc and stretches the vertebrae longitudinally, promoting fluid imbibition between the separated vertebrae and reinforcing the spine's normal shape.

The simultaneous inflation of the bladders will add a linear component to the angular joint separation, thus elongating the arc while the vertebra 18 remain separated. More particularly, as the spine 20 is lifted into the hyperlordotic arc, adjacent vertebrae 18, are gently spread apart in a longitudinal direction. The dual vectored pneumatic force of both bladders causes active angular and linear joint separation. The result is that a "bellows-like" or "sponge-like" action of the intervertebral discs is activated, producing fluid transfer and which lubricates and feeds the joints. In other words, the porous discs between the vertebrae 18 become less compressed and will actively absorb surrounding fluid by suction, or "sponge effect".

In the example shown in the Figures, the device 10 is intended to "work" i.e. exercise and separate, the lumbar spinal region 56, or more particularly, the natural lordotic arc of the lumbar spine 56. However, it should be appreciated that the device 10 can be configured to exercise other portions of the spine 20, for example, the cervical spinal region 58.

The frame 12 of the device 10 shown in the Figures is adapted for receiving a reclined person 22 such that the lumbar spine 56 is disposed over the bladders 42, 44 and the cervical spine 58 is disposed over an additional element 66 for exercising the cervical spinal region. The element 66 for exercising the cervical spinal region 58 may be a device such as disclosed in U.S. Pat. No. 5,382,226 to Graham entitled Inflatable Cervical Traction and Exercising Device, or a device such as disclosed in U.S. patent application Ser. No. 08/681,889, now U.S. Pat. No. 5,713,841 to Graham, entitled Inflatable Cervical, Cervico-Thoracic, Thoraco-Lumbar and Lumbar Exercising Device, both of which are incorporated herein by this specific reference thereto. It should be appreciated that alternatively, the element 66 may be a dual bladder vectored pneumatic joint separator 10 as described herein but modified as appropriate for exercising the cervical spinal region 58.

It is known that without the proper forward curvature naturally found in a healthy lumbar spine 56, a human being 22 can become physically disabled and unable to walk upright without pain. Such disability may become more pronounced with age as the discs in the spine gradually degenerate and the spine loses flexibility. Use of the device 10 in accordance with the present invention will train the spine into its natural shape and maintain lubrication of the intervertebral discs. The present invention increases spinal health by allowing the spine to remain more flexible than otherwise possible with conventional traction devices, orthopedic pillows or calisthenics. Further, with consistent usage, the present invention may actually reinstate a natural lordotic arc in a user's spine and more generally, may reinforce a the spine's normal shape both laterally and longitudinally.

Accordingly, a method for exercising a spine to promote spinal health is also provided by the present invention. The method generally comprises the steps of (a) separating vertebrae in a user's spine by applying a first direction of angular force to the spine in order to lift the user's spine into a lordotic arc, and subsequently applying a second direction of angular force to the user's spine to increase the arc and gently separate the vertebrae and (b) promoting fluid imbibition throughout the vertebrae by allowing the vertebrae to remain separated for a selected time. In addition, the method may comprise the step of repeating the steps of applying the angular forces on a timely basis.

For example, the device 10 described above is suitable for accomplishing the method of the present invention. The method of the present invention may therefor comprise the steps of separating vertebrae in a user's spine by applying a lifting force to the spine in order to lift and hold the spine in a lordotic arc, for example, by inflating a first bladder in a first direction against the spine, and subsequently applying a separating force to the spine being lifted and held, for example by inflating a second bladder in a second direction against the spine, in order to further lift and gently increase the lordotic arc. Next, the method includes the step of promoting fluid imbibition throughout the vertebrae by allowing the vertebrae to remain separated for a selected time.

The method further includes the step of deflating the bladders and allowing the spine to rest against the deflated bladders for a selected period of time and then repeating, on a timely basis, the steps of separating the vertebrae and promoting fluid imbibition.

Preferably, the method comprises the steps of (a) separating vertebrae in a spine by pressing the spine into a lordotic arc, including the steps of (1) partially inflating a first bladder against the spine at a first angle thereto, (2) partially inflating a second bladder against the spine at a second angle thereto, said first angle and said second angle being divergent from each other, and (3) further or fully inflating both partially inflated bladders against the spine in order to increase and elongate the lordotic arc. Next, the method includes the step of (b) promoting fluid imbibition throughout the vertebrae and intervertebral discs of the spine by allowing the vertebrae to remain separated and elongated for a selected time during the further inflation of the bladders. An additional step (c) of deflating, during a selected time, the first and second bladders is included. In one embodiment of the invention, steps (a)–(c) are repeated on a timely basis in order to reinstate the natural lordotic arc in the spine as well as establish proper linear alignment of the vertebrae.

Through such repetition, the spine and surrounding tissue receive a workout promoting cellular and fluid exchange in and around the intervertebral discs and the lordotic arc is reinforced into the spine. It is known that vertebrae contain numerous pores into which the nutrient dense fluid surrounding the spinal column can be drawn. The fluid will also be absorbed into the intervertebral discs, inhibiting dehydration thereof. It has been found that the present invention also promotes proper linear alignment of vertebrae along the spine by causing longitudinal stretching thereof. Thus, the present invention promotes spinal longitudinal and lateral shaping to achieve the proper balance and distribution of weight along the intervertebral discs.

As a specific example that should not be considered as limiting the present invention, a method for exercising a spine to promote spinal health may include the following steps. After a user is reclined or otherwise positioned with the bladders facing the lumbar spine (or alternatively the cervical spine), the first bladder is inflated partially to a pressure sufficient for lifting the spine, for example, to about 65% of total pressure, said total pressure being about five pounds. Next, the second bladder is partially inflated to a pressure sufficient for further lifting and gently arching the spine, for example, to about 65% of total pressure, said total pressure being about five pounds. Both bladders are then further inflated, up to full inflation simultaneously (in this example, about five pounds of pressure for each bladder) to increase the arc and separate the vertebrae, stretch the spine longitudinally and promote proper linear alignment of the vertebrae along the spinal axis. The bladders are then fully deflated and the inflation steps (i.e. sequential partial inflation of the first and second bladders and then full inflation of both bladders) are repeated one or several times. This repetition of steps may last about 7 to about 10 or more seconds. The bladders are then held in the further inflated state for about 5 to about 15 seconds. During the next about 10 to about 12 seconds the bladders are both fully deflated. Each of the above steps in this example is repeated for about the next ten to about fifteen minutes. To complete the therapy session, the initial steps of inflating the first and second bladders to lifting pressure and subsequently up to full inflation, are repeated and the bladders are held in the fully inflated state against the spine for another about 3 minutes to about 15 minutes.

It is noted that the timing and inflation pressures of the bladders may be programmed into a computer such that the therapy session can be operated automatically. Of course, the inflation can alternatively be done manually by the user or a physical therapist, by using a hand pump.

Although there has been hereinabove described a vectored pneumatic joint separator and method, in accordance with the present invention, for purposes of illustrating the manner in which the invention may be used to advantage, it will be appreciated that the invention is not limited thereto. Accordingly, any and all modifications, variations, of equivalent arrangements which may occur to those skilled in the art should be considered to be within the scope of the present invention.

What is claimed is:

1. A spinal joint separator device comprising:

a frame having an arched projection thereon, said arched projection generally conforming to a curvature of the lower thoracic and lumbar vertebrae of a human spine and having a first surface generally conforming to the lower thoracic vertebrae curvature and a second surface generally conforming to the lumbar vertebrae curvature; and means, secured to the frame, for separating the lower thoracic and lumbar vertebrae in the spine in order to promote fluid imbibition therethrough and promote spinal lateral and longitudinal shaping, said means for separating including:

first inflatable bladder means, disposed on said first surface, for directly bearing against the lower thoracic vertebrae of the spine in a first direction; and second inflatable bladder means disposed on said second surface, for directly bearing against the lumbar vertebrae of the spine in a second direction, said first and second directions being divergent along a sagittal plane of the user.

2. The device according to claim 1 further comprising means for enabling independent and sequential inflation of the first and second bladder means.

3. The device according to claim 1 wherein the second bladder means overlaps the first bladder means and wherein the device further comprises means for enabling inflation of the first bladder means prior to and independently of inflation of the second bladder means.

4. A spinal joint separator device comprising:

a frame having an arched projection thereon, said arched projection generally conforming to a curvature of the lower thoracic and lumbar vertebrae of a human spine and having a first surface generally conforming to the lower thoracic vertebrae curvature and a second surface generally conforming to the lumbar vertebrae curvature; and means, secured to the frame, for separating the lower thoracic and lumbar vertebrae in the spine in order to increase a lordotic arc in the spine and promote fluid imbibition therethrough, said means for separating including first inflatable bladder means for directly applying a lifting force against the lower thoracic vertebrae in the spine, and second inflatable bladder means for directly applying a separating force vector against the lumbar vertebrae in the spine, said separating force vector being in a direction away from the lifting force vector.

5. The device according to claim 4 wherein the device further comprises means for independently controlling inflation of the bladder.

6. The device according to claim 5 wherein the second inflatable bladder overlaps the first inflatable bladder.

7. A spinal joint separator device for promoting spinal health, said device comprising:

a frame having an arched projection thereon, said arched projection generally conforming to a curvature of the lower thoracic and lumbar vertebrae of a human spine and having a first surface generally conforming to the lower thoracic vertebrae curvature and a second surface generally conforming to the lumbar vertebrae curvature;

means, including a first bladder secured to the frame, for accentuating a lordotic arc in a region of the spine and causing angular separation of vertebrae in the region;

means, including a second bladder secured to the frame and overlapping the first bladder, for linearly elongating the lordotic arc while the vertebrae are angularly separated by the first bladder; and means for enabling independent inflation and simultaneous inflation of the first and the second bladders.

* * * * *